US009795208B1

(12) United States Patent
Toder

(10) Patent No.: US 9,795,208 B1
(45) Date of Patent: Oct. 24, 2017

(54) SYSTEM AND METHOD FOR CREATING A TEMPORARY LIFT OF THE FACE AND NECK

(76) Inventor: Ellis Toder, Huntingdon Valley, PA (US)

( * ) Notice: Subject to any disclaimer, the term of this patent is extended or adjusted under 35 U.S.C. 154(b) by 2159 days.

(21) Appl. No.: 12/617,694

(22) Filed: Nov. 12, 2009

(51) Int. Cl.
*A61F 5/08* (2006.01)
*A45D 44/22* (2006.01)
*A61N 1/32* (2006.01)

(52) U.S. Cl.
CPC ............. *A45D 44/22* (2013.01); *A61N 1/328* (2013.01)

(58) Field of Classification Search
CPC ................................ A45D 44/22; A61N 1/328
USPC ................ 606/204.35, 44; 351/123; 24/3.13; 602/17
See application file for complete search history.

(56) References Cited

U.S. PATENT DOCUMENTS

| | | | |
|---|---|---|---|
| 1,563,767 A | 12/1925 | MacDonald | |
| 2,068,777 A * | 1/1937 | Teal | 606/204.35 |
| 2,079,128 A * | 5/1937 | McKinlay | 606/204.35 |
| 3,154,071 A * | 10/1964 | Haagen | 606/204.35 |
| 3,695,257 A * | 10/1972 | Hale | 606/204.35 |
| 3,709,234 A * | 1/1973 | Seerahn | 132/214 |
| 3,736,925 A * | 6/1973 | Erman | 606/204.35 |
| 4,250,880 A * | 2/1981 | Gordon | 604/180 |
| 4,727,881 A * | 3/1988 | Craighead et al. | 600/392 |
| 4,949,733 A * | 8/1990 | Sampson | 128/864 |
| 5,582,585 A * | 12/1996 | Nash-Morgan | 604/44 |
| 2009/0171385 A1 | 7/2009 | Karnwie-Tuah | |

* cited by examiner

*Primary Examiner* — Richard Louis
(74) *Attorney, Agent, or Firm* — LaMorte & Associates P.C.

(57) ABSTRACT

A system and method of temporarily lifting sections of skin on and about the face and neck proximate the ear so as to produce a facelift effect. An application template is provided that can be hung around the ear. At least two sections of tape are provided. One section of tape is connected to the top end of the application template. A second section of tape is connected to the bottom end of the application template. The application template orients both sections of tape. Once the sections of tape are adhered to the skin, the application template is removed. An elastic element is then joined between the sections of tape an creates a tension force that causes the tape to pull the skin toward the ear.

6 Claims, 4 Drawing Sheets

SYSTEM AND METHOD FOR CREATING A TEMPORARY LIFT OF THE FACE AND NECK

BACKGROUND OF THE INVENTION

1. Field of the Invention

In general, the present invention relates to systems and methods that temporarily alter the position of the skin on and around the face and neck by physically pulling upon the skin. More particularly, the present invention relates to systems and methods that apply tape to the skin and apply pulling forces to the tape to achieve the effects of a facelift or necklift.

2. Prior Art Description

It is well known that as a person ages, that person's skin becomes less elastic. Consequently, skin in certain areas of the body tends to wrinkle, sag and/or pull away from the underlying muscle tissue. Such sagging of the skin commonly occurs around the eyes, cheeks, and neck.

In an attempt to correct the sagging of the skin, many people undergo cosmetic surgery. During a cosmetic surgical procedure, skin is pulled taut against the underlying muscle tissue. The skin is surgically sewn into place and the excess skin is usually removed. Such surgical procedures are commonly referred to as facelifts or neck lifts.

Although cosmetic surgery is commonplace, it still involves the risks inherent in all surgeries. Surgical sites are prone to swelling, bruising, and infection. Furthermore, the end result of the surgery may not be as aesthetically pleasing as a person may have hoped. Lastly, cosmetic surgery is expensive and is rarely covered by insurance because most cosmetic surgical procedures are not medically necessary.

Recognizing the many disadvantages of cosmetic surgery, many people attempt to treat areas of sagging skin using non-surgical methods. Many non-surgical methods exist for treating areas of sagging skin. For instance, creams are used to moisturize the skin and increase the elasticity of the skin. However, the present invention is concerned with systems that temporarily improve the appearance of an area of skin by physical manipulation.

U.S. Pat. No. 1,563,767 to MacDonald, entitled Facial Device, shows an early attempt to temporarily create a facelift using physical manipulation. In the MacDonald patent, patches of adhesive are attached to the face. The patches of adhesive are joined together by a strap. The strap is tightened so that the adhesive patches, and the skin they engage, are pulled toward one another. This lifts the skin and creates the desired aesthetic effect.

U.S. Pat. No. 3,736,925 to Erman, entitled Face-Lifting Apparatus, shows a system where multiple pieces of tape are attached to the skin of the face. All the pieces of tape are attached to a single tether that wraps around the back of the head. The tether is tightened to pull up on the tape and the skin attached to the tape.

U.S. Patent App. Pub. No. 2009/0171385 to Karnwie-Tuah, entitled Facelift Device, discloses pieces of adhesive tape that attach to the skin of the face. The pieces of tape are attached to large loops that pass around the ears. The large loops are interconnected by a strap. The strap is tightened to lift both the ears and the skin attached to the tape.

The obvious problem of such prior art facelift systems is the use of a strap or tether that passes around the back of the head. Even if the strap or tether were the exact color of a person's hair, it would be impossible to hide. The strap or tether mats down the hair and prevents the hair from moving freely as the hair moves. As such, the mentioned prior art systems are highly noticeable and are only practical for people who wear wigs and can hide the strap or tether under the structure of a wig.

Wigs, hairpieces and the like are becoming less popular. As such, a need therefore exists for a system that applies tape to the skin and applies tension to the tape, without the use of a strap or tether that passes over the head and/or the hair. A need also exists for a face and neck lift system where the presence of the system, while worn on the body, is highly discrete and cannot be noticed by casual observation. These needs are met by the present invention as described and claimed below.

SUMMARY OF THE INVENTION

The present invention is a system and method of temporarily lifting sections of skin on and about the face and neck, proximate the ear so as to produce a facelift and necklift effect. An application template is provided. The application template is shaped and sized so that it can be hung around the ear. Once hung around the ear, the application template has a top end that terminates adjacent to the front of the ear and a bottom end that terminates near the rear of the jawbone.

At least two sections of tape are provided. One section of tape is connected to the top end of the application template. A second section of tape is connected to the bottom end of the application template. The application template orients both sections of tape during the application of the tape to the skin. Accordingly, when the tape is adhered to the skin, one section of tape adheres to the face in front of the ear. The other section of tape adheres near the rear of the jawbone.

Once the sections of tape are adhered to the skin, the application template is removed. An elastic element is then joined between the sections of tape. The elastic element is looped around the rear of the ear. The elastic element is sized so that it has to stretch slightly to reach between the sections of tape. The stretching of the elastic element causes the elastic element to apply a tension force to the sections of tape. The tension force pulls on the tape and causes the tape to pull the skin toward the ear. This lifts the skin and creates the desired cosmetic effect.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Although the present invention system can be embodied in many ways, the primary embodiment being illustrated shows the system using a minimal number of adhesive pads. This embodiment is selected for the sake of simplicity and in order to set forth the best mode contemplated for the invention. The illustrated embodiment, however, is merely exemplary and should not be considered a limitation when interpreting the scope of the appended claims.

Figure 1:
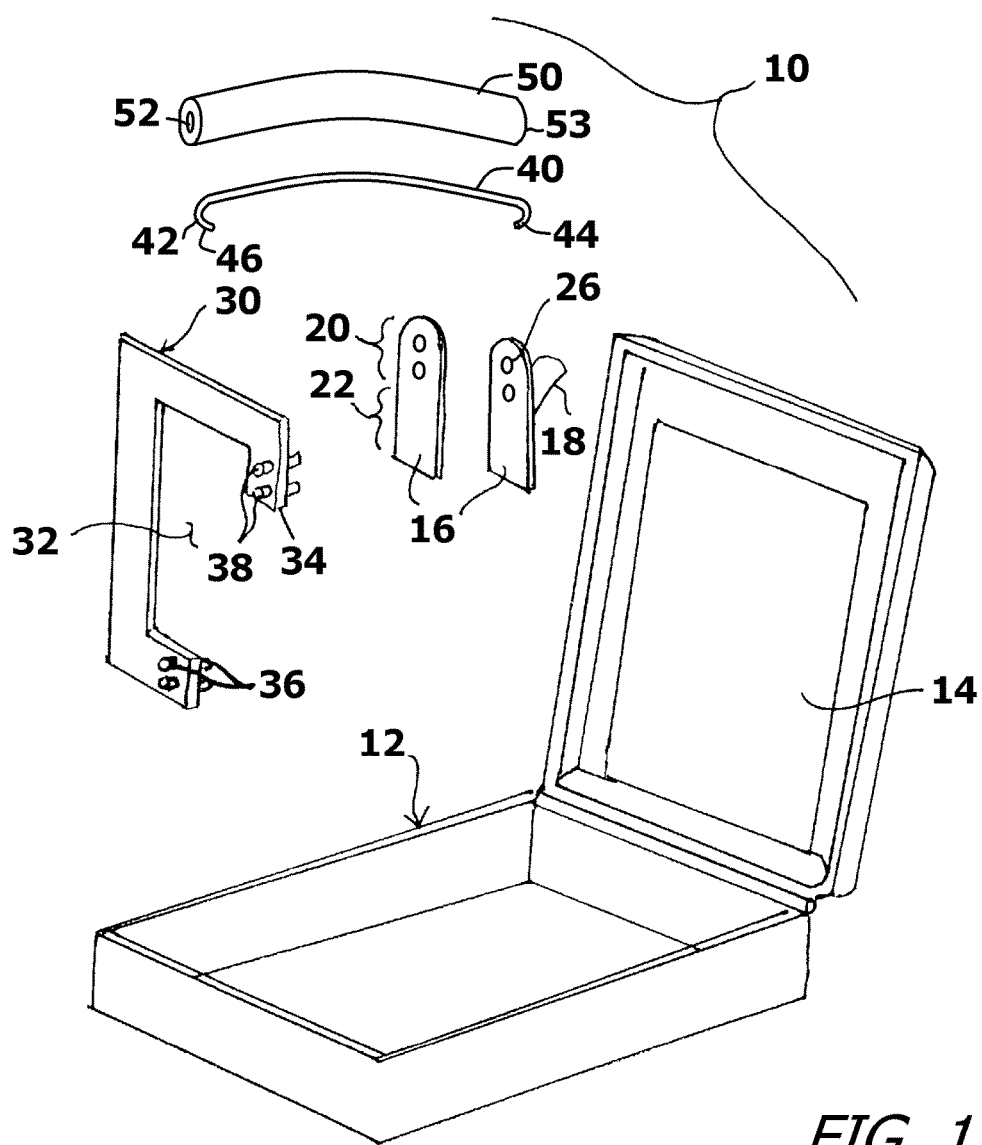
FIG. 1 is a perspective exploded view of an exemplary embodiment of a kit containing the present invention system.

Referring to FIG. 1, a temporary skin lift system 10 is shown that is packaged in a common housing 12. The housing 12 preferably holds a mirror 14 that can be used to help apply the components contained within the lift system 10. The housing 12 may also contain a light that is activated by the opening of the housing 12. Likewise, the housing may contain a small music circuit that plays music when the housing is opened.

Precut segments of tape 16 are provided within the lift system 10. The segments of tape 16 are adhered to peel-way substrates 18 to prevent the segments of tape 16 from becoming contaminated prior to use. Each segment of tape 16 is preferably transparent and is generally rectangular in shape. Each segment of tape 16 has a tab section 20 and an adhesive section 22. The adhesive section 22 is coated in a tacky adhesive (not shown) that will adhere to human skin. The tab section 20 does not contain adhesive. The tab section 20 is perforated and therefore defines at least one engagement hole 26. In the shown embodiment, each segment of tape 16 contains two engagement holes 26. However, it should be understood that any number of engagement holes 26 may be present.

An application template 30 is provided. The application template 30 is a structure of plastic or paperboard that is generally C-shaped so as to define a central opening 32. The central opening 32 is sized to receive the average human ear so the application template 30 can fit around the average human ear. The application template 30 has two ends, the upper end 34 and the lower end 36. The upper end 34 contains position pegs 38 that extend both forward and backward from the main plane of the application template 30. The position pegs 38 correspond in number, size and orientation to the engagement holes 26 that are present in the tab section 20 of each segment of tape 16. The position pegs 38, therefore, create an orientation key. It will be understood that the engagement holes 26 in the segments of tape 16 can receive the positioning pegs 38 on the application template 30 only when the segments of tape 16 are properly aligned in relation to the application template 30.

An elastic element 40 is provided. The elastic element 40 has a length of between two and four inches when unstretched. The elastic element 40 is preferably pigmented in a flesh tone so as be camouflaged when viewed against a person's skin. The elastic element 40 has a first end 42 and an opposite second end 44. Both the first end 42 and the second end 44 are terminated with a small hook or equivalent mechanical fastener 46. It will be understood that the elastic element 40 shown can be replaced with a segment of an elastic band or any other flexible length of elastic material.

A tubular cushion 50 is provided. The tubular cushion 50 is preferably made from an elastomeric material, such as silicon, latex or foam rubber. However, sewn tubes of plush material can also be used. The tubular cushion 50 has an outside diameter of approximately ¼ inch or less. This enables the tubular cushion 50 to comfortably rest behind the ear. The tubular cushion 50 is preferably flesh colored so as to be camouflaged when viewed against a person's skin.

The tubular cushion 50 is hollow and has two open ends 52, 53. The elastic element 40 extends through the tubular cushion 50. However, the elastic element 40 is free moving within the tubular cushion 50 and is not bonded to the tubular cushion 50.

Figure 2:
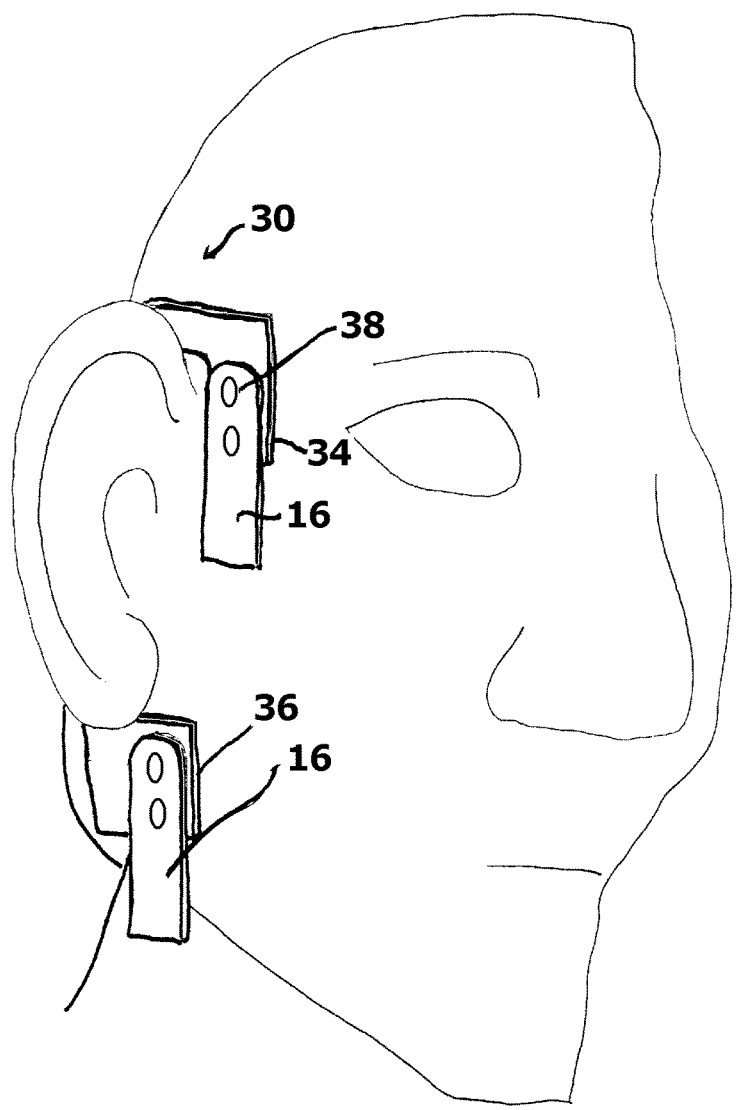
FIG. 2 shows the application template applied over the ear of a person using the present invention system.

Referring now to FIG. 2, in conjunction with FIG. 1, the method of using the lift system 10 can be explained. The application template 30 is placed over the ear. The purpose of the application template 30 is to guide the placement of the segments of tape 16. Once the application template 30 is positioned around the ear, the upper end 34 terminates in front of the ear. The lower end 36 terminates near the back of the jawbone. Two segments of tape 16 are connected to the application template 30 before the application template 30 is placed around the ear. One segment of tape 16 is attached to the position pegs 38 at the lower end 36 of the application template 30. Likewise, one segment of tape 16 is attached to the position pegs 38 at the upper end 34 of the application template 30. The protective peel-away substrates 18 are left on the segments of tape 16. The application template 30 and the two attached segments of tape 16 are then placed around the ear.

The application template 30 orients the segments of tape 16 so that one piece of tape is oriented over the skin near the temple and one piece of tape is oriented near the rear of the jawbone. Once in these positions, the user peels the protective substrates 18 away from the segments of tape 16 and adheres the segments of tape 16 to the skin. This condition is captured by FIG. 2. Once the segments of tape 16 are attached to the skin, the segments of tape 16 are disconnected from the application template 30 and the application template 30 is removed from around the ear.

Figure 3:
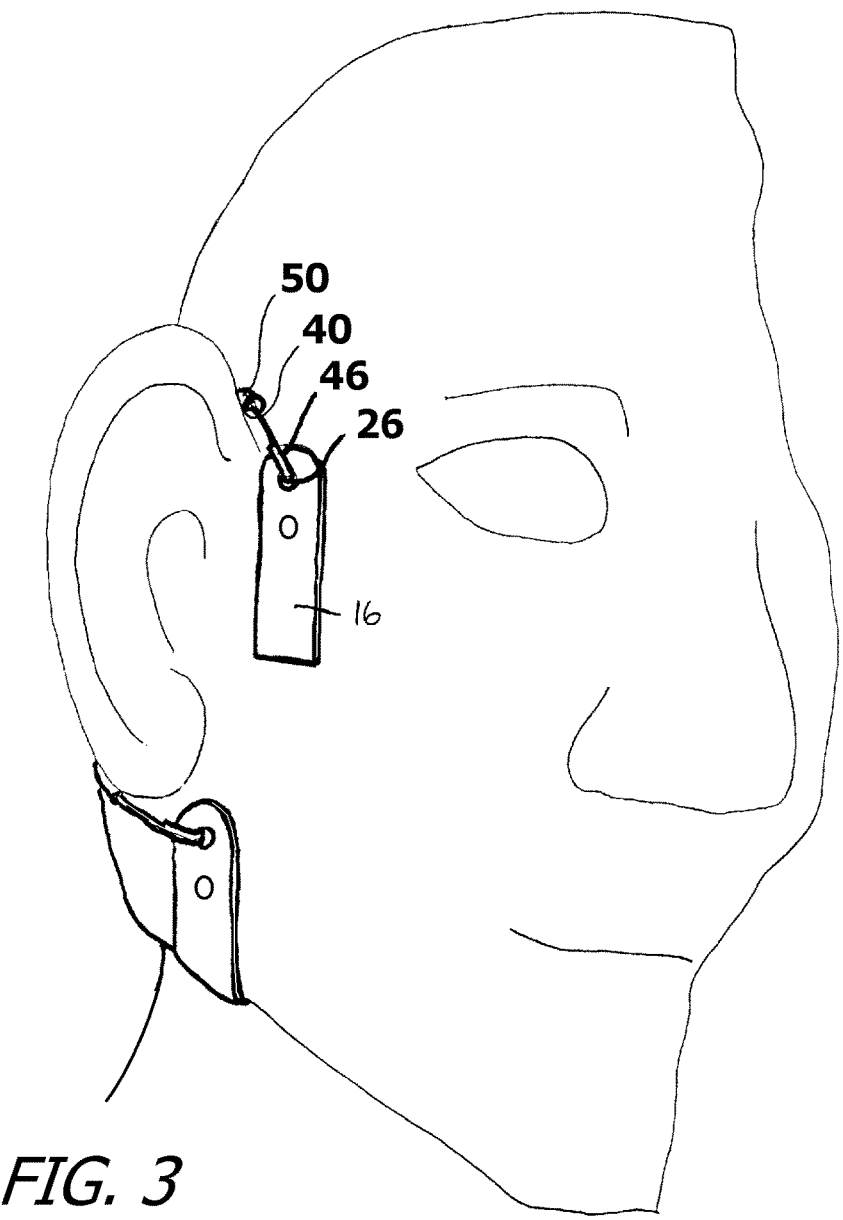
FIG. 3 shows the present invention system being used to create a facelift and necklift through physical manipulation of the skin.

Referring to FIG. 3 in conjunction with FIG. 2, it can be seen that the elastic element 40 is advanced through the tubular cushion 50. The mechanical fasteners 46 at the ends of the elastic element 40 are engaged with the engagement holes 26 in the segments of tape 16. The elastic element 40 and the surrounding tubular cushion 50 are placed behind the ear. The tubular cushion 50 prevents the elastic element 40 from contacting the skin behind the ear. The distance from one segment of tape 16 to another across the back of the ear is, on average, longer than is the length of the elastic element 40. The elastic element 40 must, therefore, stretch to reach between the segments of tape 16. Each segment of tape 16 has two engagement holes 26. The mechanical fasteners 46 at the ends of the elastic element 40 can be hooked into either of the engagement holes 26 as elected by a user. As a result, the degree of tension present in the elastic element 40 can be selectively increased or decreased.

Since the elastic element 40 is stretched as it passes behind the ear, the elastic element 40 applies a tension force to both segments of tape 16. The tension force created by the elastic element 40 is transferred to the segments of tape 16 and then to the skin. As a result, the skin under the segment of tape 16 is pulled toward the ear. The result is that the skin under and around the segments of tape 16 is lifted toward the ear, creating the same result as a surgical facelift and necklift without the need for surgery.

The segments of tape 16 are preferably transparent and are very difficult to detect visually once applied to the skin. The elastic element 40 is very thin and is colored the pigment of skin. Furthermore, the elastic element 40 lay in the areas of the head that are commonly covered by a person's hair. Consequently, the elastic element 40 is difficult to detect visually. Lastly, the tubular cushion 50 lies behind the ear. As such, the tubular cushion 50 is difficult to visually detect. The result is a temporary facelift system 10 that is difficult for a casual observer to detect.

To remove the system, the elastic element 40 is unhooked from the two segments of tape 16. The elastic element 40 and the surrounding tubular cushion 50 are removed. The two segments of tape 16 are then peeled away from the skin.

In the exemplary embodiment that is illustrated, the application template 30 is configured to position only two segments of tape 16. Likewise, the elastic element 40 has only two hooks for interconnecting only two segments of tape 16. It will be understood that the use of only two segments of tape 16 is merely exemplary and that any plurality of tape segments 16 can be used.

Figure 4:
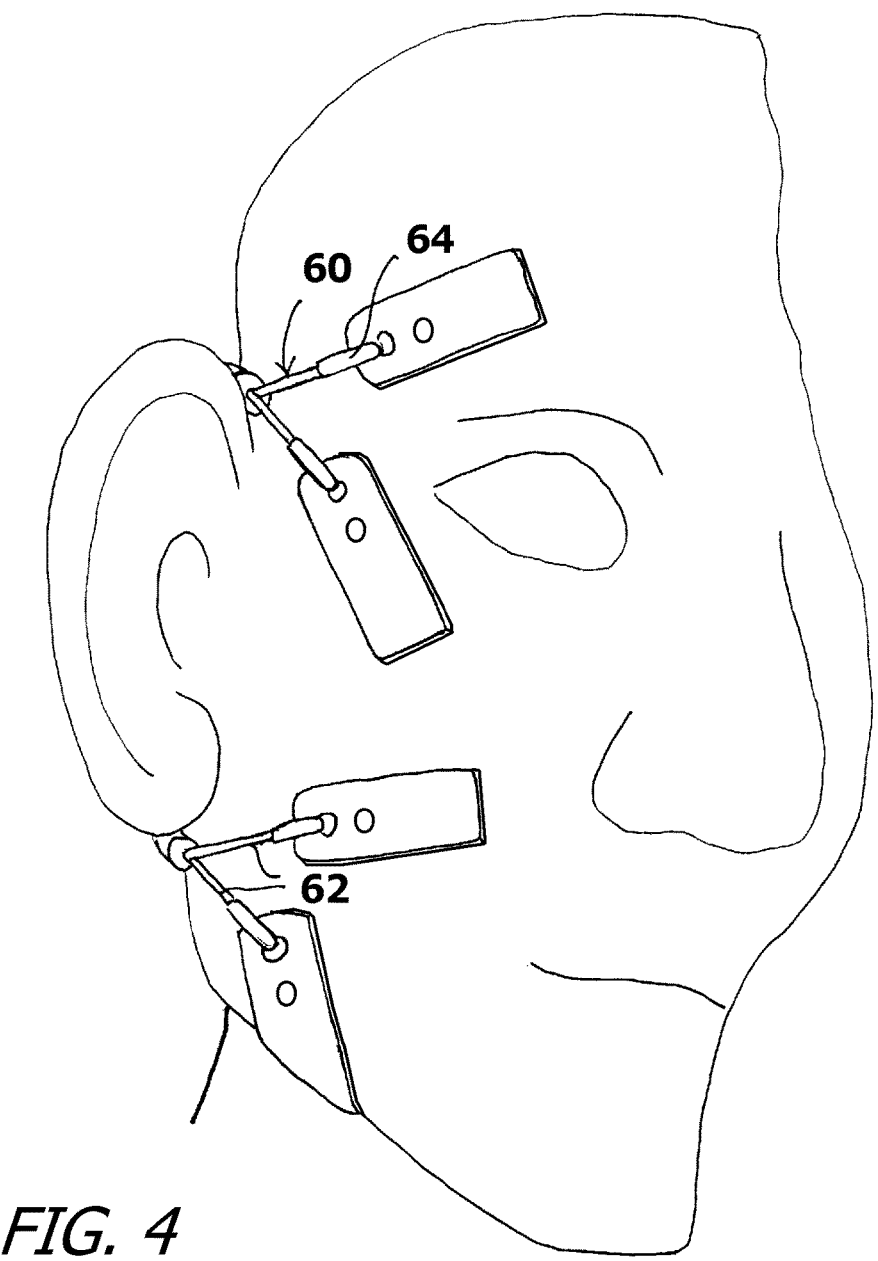
FIG. 4 shows an alternate embodiment of the present invention system.

Referring to FIG. 4, such an alternate embodiment is shown. In FIG. 4, it can be seen that the elastic element 60 is split at both ends into branch arms 62. Each of the branch arms 62 terminates with a hook or similar mechanical fastener 64. Multiple segments of tape 16 are provided. Each segment of tape 16 attaches to a separate branch arm 62 of the elastic element 60. The elastic element 60 passes over the back of the ear. Skin can therefore be pulled toward the ear at multiple locations. It will also be understood that the structure of the application template (not shown) can be altered to match the configuration of the elastic element 60 and the number of segments of tape 16 being applied.

The embodiments of the present invention that are illustrated and described are merely exemplary and a person skilled in the art can make many variations to those embodiments. For instance, the shape of the segments of tape can be altered. The positions where the tape is adhered to the skin can be altered. The connection mechanism that interconnects the segments of tape to the elastic element can be most any mechanical fastener. Lastly, the elastic element can be varied in length and elasticity. All such embodiments are intended to be included within the scope of the present invention as defined by the claims.

What is claimed is:

1. A method of temporarily lifting sections of skin on and about the face and neck proximate the ear, said method comprising the steps of:
   providing an application template;
   providing a first segment of tape;
   providing a second segment of tape;
   attaching said first segment of tape and said second segment of tape to said application template and hanging said application template around said ear, wherein said application template orients said first segment of tape over a first section of skin, and said application template orients said second section of tape over a second segment of skin;
   adhering said first segment of tape to said first section of skin;
   adhering said second segment of tape to said second section of skin;
   providing an elastic element having a first end, a second end and a central section between said first end and said second end;
   providing a soft tubular cushion having a first open end and a second open end;
   extending said elastic element through said soft tubular cushion, wherein said soft tubular cushion surrounds at least a portion of said central section of said elastic element, and wherein said elastic element is free to move independently within said soft tubular cushion;
   attaching said first end of said elastic element to said first segment of tape;
   attaching said second end of said elastic element to said second segment of tape; and
   looping said central section of said elastic element behind said ear, wherein said elastic element stretches through said soft tubular cushion and applies a tension force between said first segment of tape and said second segment of tape that biases said soft tubular cushion against said ear, wherein said soft tubular cushion pads contact between said elastic element and said ear.

2. A method of temporarily lifting sections of skin proximate the ear, said method comprising the steps of:
   providing a first tape segment a second tape segment and a template;
   connecting said first tape segment and said second tape segment to said template;
   placing said template about the ear, therein orientating said first tape segment and said second tape segment relative said ear;
   adhering said first tape segment and said second tape segment to the skin;
   removing said template;
   providing an elastic element;
   providing a soft tubular cushion having a first open end and a second open end;
   extending said elastic element through said soft tubular cushion, wherein said soft tubular cushion surrounds at least a portion of said elastic element, and wherein said elastic element is free to move independently within said soft tubular cushion;
   positioning said soft tubular cushion behind said ear; and
   extending said elastic element from said first tape segment to said second tape segment, wherein said elastic element stretches through said soft tubular cushion and applies a tension force to both said first tape segment and said second tape segment that biases said soft tubular cushion against said ear, wherein said soft tubular cushion pads contact between said elastic element and said ear.

3. The method according to claim 2, wherein said step of providing a first tape segment, a second tape segment and a template includes providing a first tape segment containing at least one first alignment hole, providing a second tape segment containing at least one second alignment hole, and providing a template having alignment posts that engage said at least one first alignment hole and said at least one second alignment hole, therein orienting said first tape segment and said second tape segment relative said template.

4. The method according to claim 3, wherein said elastic element is terminated with mechanical fasteners, wherein said step of extending said elastic element behind said ear from said first tape segment to said second tape segment includes engaging said at least one first alignment hole and said at least one second alignment hole with said mechanical fasteners.

5. The method according to claim 3, wherein said template defines a central opening and said step of placing said template about the ear includes placing said ear within said central opening.

6. A method of temporarily lifting sections of skin proximate the ear, said method comprising the steps of:
   attaching tabs to an application template and hanging said application template around said ear, wherein said application template orients said tabs over said sections of skin
   adhesively attaching said tabs to said sections of skin;
   connecting said tabs to opposite ends of an elastic element;
   passing a soft tubular cushion around at portion of said elastic element, wherein said elastic element is free moving within said soft tubular cushion; and
   placing said soft tubular cushion in contact with said ear behind said ear;

wherein said elastic element stretches and applies a tension force to said tabs that biases said sections of skin toward said ear and biases said soft tubular cushion against said ear.

\* \* \* \* \*